US011058500B2

(12) United States Patent
D'Amelio et al.

(10) Patent No.: US 11,058,500 B2
(45) Date of Patent: Jul. 13, 2021

(54) ROBOT-ASSISTED SURGICAL GUIDE SYSTEM FOR PERFORMING SURGERY

(71) Applicant: Epica International, Inc., San Clemente, CA (US)

(72) Inventors: Frank D'Amelio, San Clemente, CA (US); Damiano Fortuna, Rignano Sull'Arno (IT); Leonardo Manetti, Montevarchi (IT); Denis Mattia De Micheli, Navacchio di Cascina (IT); Gianluca Parrini, Cascina (IT)

(73) Assignee: Epica International, Inc., San Clemente, CA (US)

(*) Notice: Subject to any disclaimer, the term of this patent is extended or adjusted under 35 U.S.C. 154(b) by 177 days.

(21) Appl. No.: 16/160,575

(22) Filed: Oct. 15, 2018

(65) Prior Publication Data
US 2019/0110846 A1 Apr. 18, 2019

Related U.S. Application Data

(60) Provisional application No. 62/572,986, filed on Oct. 16, 2017, provisional application No. 62/627,565, filed on Feb. 7, 2018.

(51) Int. Cl.
*A61B 34/32* (2016.01)
*A61G 13/10* (2006.01)
*A61B 34/20* (2016.01)
*A61B 6/04* (2006.01)
*A61B 5/055* (2006.01)
(Continued)

(52) U.S. Cl.
CPC ............ *A61B 34/32* (2016.02); *A61B 5/055* (2013.01); *A61B 6/0407* (2013.01);
(Continued)

(58) Field of Classification Search
CPC ............ A61B 90/11; A61B 2017/3405; A61B 2017/3409; A61B 2017/3411
See application file for complete search history.

(56) References Cited

U.S. PATENT DOCUMENTS 6,400,979 B1 * 6/2002 Stoianovici ............ A61B 90/36
600/427
6,436,035 B1 8/2002 Toth et al.
(Continued)

FOREIGN PATENT DOCUMENTS

WO 2017134546 A2 8/2017

OTHER PUBLICATIONS

PCT International Search Report and Written Opinion dated Jan. 2, 2019 in corresponding PCT Application No. PCT/US2018/055951 filed Oct. 15, 2018 (EPICA International Inc.).

*Primary Examiner* — Elizabeth Houston
*Assistant Examiner* — Lindsey Bachman
(74) *Attorney, Agent, or Firm* — Steptoe & Johnson LLP; Robert Greenfeld

(57) ABSTRACT

A surgical system includes a bed extending along a main direction, a robotic arm disposed adjacent to the bed, and a surgical guide attached to the robotic arm. The bed has a table top to support a patient, the robotic arm is controllable to move in relation to the body of the patient; and the surgical guide is capable of holding a surgical instrument and measuring a translation of the surgical instrument as it moves through the surgical guide. The robotic arm is configured to position the surgical guide to a desired position in relation to a target area of the patient.

14 Claims, 13 Drawing Sheets

(51) Int. Cl.

| | |
|---|---|
| *A61B 17/34* | (2006.01) |
| *A61B 90/00* | (2016.01) |
| *A61B 90/11* | (2016.01) |
| *A61B 34/30* | (2016.01) |
| *A61B 6/00* | (2006.01) |
| *A61B 90/98* | (2016.01) |

(52) U.S. Cl.
CPC .......... *A61B 17/3476* (2013.01); *A61B 34/20* (2016.02); *A61B 34/30* (2016.02); *A61B 90/06* (2016.02); *A61B 90/11* (2016.02); *A61G 13/10* (2013.01); *A61B 6/4435* (2013.01); *A61B 90/98* (2016.02); *A61B 2034/2055* (2016.02); *A61B 2034/2059* (2016.02); *A61B 2090/062* (2016.02); *A61B 2090/064* (2016.02); *A61B 2090/374* (2016.02); *A61B 2090/3762* (2016.02)

(56) References Cited

U.S. PATENT DOCUMENTS

| | | | |
|---|---|---|---|
| 9,687,982 B1* | 6/2017 | Jules | B25J 9/161 |
| 2007/0250006 A1* | 10/2007 | Court | A61B 90/06 |
| | | | 604/117 |
| 2008/0064921 A1 | 3/2008 | Larkin et al. | |
| 2009/0171184 A1* | 7/2009 | Jenkins | A61B 90/37 |
| | | | 600/411 |
| 2010/0125283 A1* | 5/2010 | Butcher | A61B 90/11 |
| | | | 606/130 |
| 2014/0066944 A1* | 3/2014 | Taylor | B25J 15/0466 |
| | | | 606/103 |
| 2015/0150633 A1 | 6/2015 | Castro et al. | |
| 2017/0172667 A1 | 6/2017 | Charles | |
| 2018/0049825 A1* | 2/2018 | Kwon | A61B 34/30 |

* cited by examiner

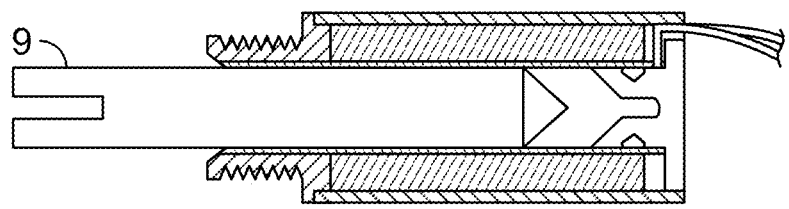
De-energised
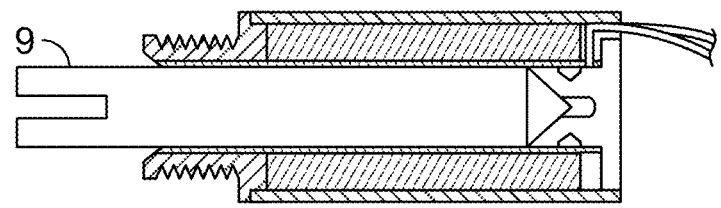
Energised
FIG. 22
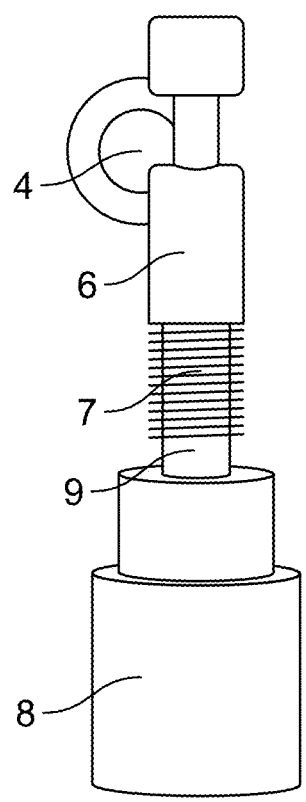
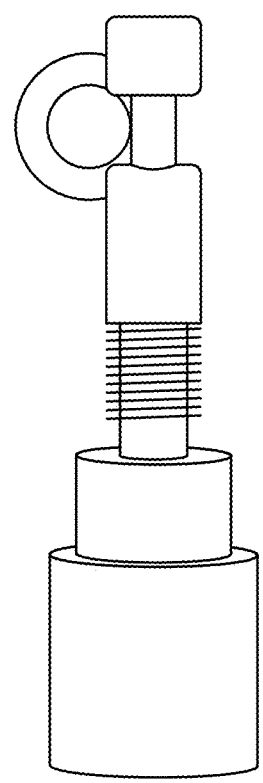
FIG. 23A  FIG. 23B

ROBOT-ASSISTED SURGICAL GUIDE SYSTEM FOR PERFORMING SURGERY

CLAIM OF PRIORITY

This application claims priority from U.S. Provisional Application No. 62/572,986, filed on Oct. 16, 2017, and from U.S. Provisional Application No. 62/627,565, filed on Feb. 7, 2018, both of which are incorporated by reference in their entireties.

FIELD

The present disclosure relates generally to the field of medical systems and, in particular, to a robot-assisted sensorized surgical guide that may be used in combination with an imaging device or system.

BACKGROUND

With any type of surgery there is a health risk to the patient. During a surgical procedure, gaining access to a target area within the body of a patient may be difficult and may require precise navigation around vital arteries and organs. What is needed is a universal assistant for a surgeon to perform safer and more efficient surgeries.

SUMMARY

Briefly, and in general terms, the present disclosure is directed to various embodiments of a system and method for performing robot-assisted surgery. The system may include a radiological imaging device or system, a bed to support a patient, a robotic arm disposed adjacent to the radiological imaging system, and a sensorized surgical guide attached to the robotic arm and that holds a surgical instrument and measures the translation of a surgical instrument along an axis of intervention and the rotation of the surgical instrument about the axis of intervention. In use, the axis of intervention point is determined and the robotic arm positions the sensorized surgical guide in line with the axis of intervention point so that the surgical instrument may be guided to the target area of the patient.

Other features and advantages will become apparent from the following detailed description, taken in conjunction with the accompanying drawings, which illustrate by way of example the features of the various embodiments.

BRIEF DESCRIPTION OF THE DRAWINGS

FIG. 22 is a schematic diagram showing the energizing of a shutter for a sensorized surgical guide, according to an embodiment of the present invention;

FIGS. 23A and 23B are schematic diagrams showing the shutter assembly of a sensorized surgical guide, according to an embodiment of the present invention.

Figure 1:
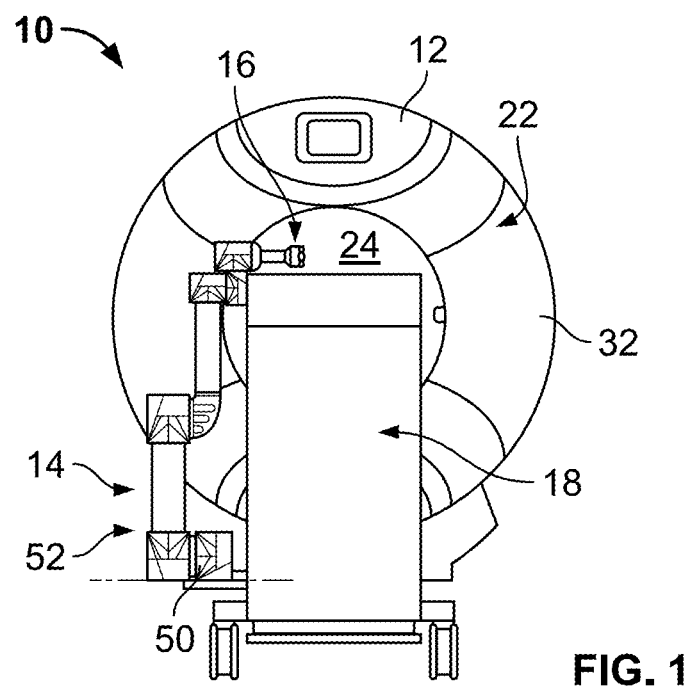
FIG. 1 shows an exemplary surgical system including a radiological imaging system and a sensorized surgical guide attached to a robotic arm, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Each of the features and teachings disclosed herein can be used separately or in conjunction with other features and teachings to provide a surgical system including a radiological imaging system with a bed. Representative examples using many of these additional features and teachings, both separately and in combination, are described in further detail with reference to the attached figures.

With reference to FIG. 1, surgical system 10 includes radiological imaging system 12, robotic arm 14, sensorized surgical guide 16, and bed 18. System 10 may be useful in both medical and veterinary applications for performing radiological imaging and robotic assisted surgeries. Radiological imaging system 12 is used to view at least a portion of a patient surrounding a target area for surgery. In various embodiments, sensorized surgical guide 16 may be used with a variety of surgical instruments relating to dissection, occlusion, retraction, grasping, energy (e.g., laser), ultrasound, cameras, and the like. The surgical instrument may be radio-opaque marked such that it is more visible using the radiological imaging system. In addition, the surgical instrument may include additional markers internally or externally indicating the length of the surgical instrument. In one embodiment, robotic arm 14 positions sensorized surgical guide 16 at a determined location and angle relative to the patient in order to allow a surgeon to use the sensorized surgical guide for a set of surgical instruments during an intervention. Sensorized surgical guide 16 may include at least one sensor to measure the translation of the any inserted surgical instrument along an axis of intervention or rotation about the axis of intervention that can be used to continuously monitor the insertion depth of the inserted surgical instrument. Thus, the radiological imaging system and sensorized surgical guide can provide constant feedback to the surgeon about the position of the inserted surgical instrument in the patient. The system may also include a display having a graphical user interface and navigation software capable of acquiring images from the radiological imaging system and referencing the position and orientation of a surgical instrument fed through the sensorized surgical guide. In another embodiment, the system may not include the radiological imaging system.

Figure 2:
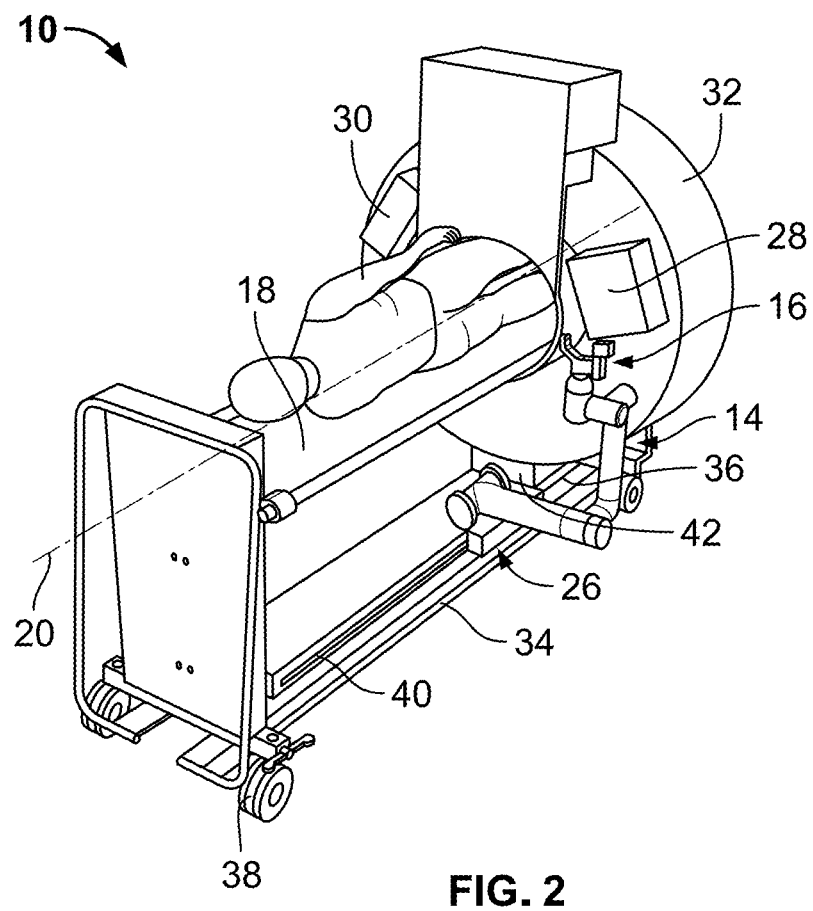
FIG. 2 shows another exemplary surgical system including a radiological imaging system and a sensorized surgical guide attached to a robotic arm, according to an embodiment of the present invention.

In particular, radiological imaging system 12 is suitable for performing radiological imaging examinations including, but not limited to, X-rays, CT scans, and fluoroscopy. In one embodiment, the imaging system includes a control unit suitable to control the radiological imaging system. Bed 18 extends along main direction 20 (shown in FIG. 2) and has a support surface for the patient. In one embodiment, radiological imaging system 12 includes a gantry 22 suitable to perform the radiological imaging of at least one portion of the patient and defining an analysis zone 24 suitable to house at least a portion of bed 18. For example, the gantry may have a circular shape as shown in FIGS. 1 and 2, which is suitable to house at least one portion of bed 18 and the patient. Further, the radiological imaging system shown in the embodiment of FIG. 2 includes a load-bearing structure 26 suitable to support gantry 22.

As shown in FIG. 2, which is a partial cut-away, gantry 22 contains various components for performing a radiological scan. Examples of the components contained in gantry 22 include, but are not limited to, the following. A source 28 suitable to emit radiation, for example X-rays. The gantry may also include at least one detector 30 suitable to receive the radiation emitted by source 28 and suitable to be positioned substantially on the opposite side of bed 18 from the source. Further, gantry 22 may include housing 32 suitable to contain at least partially the aforementioned components, and the housing may contain additional components as needed. In particular, detector 30 is suitable to detect the radiation (e.g., X-ray) that has traversed the patient's body during a scan. In one embodiment, detector 30 may include a sensing element such as a flat panel and/or a linear sensor. In further embodiments, the system may not include a gantry, and the locations of the source and detector may define the analysis zone.

As shown in the example of FIG. 2, load-bearing structure 26 includes base 34 suitable to support gantry 22. In one embodiment, the structure includes translating component 36 suitable to move gantry 22 in a sliding direction substantially parallel to main direction 20. In addition, the structure may include wheels 38, which may be pivoting wheels, suitable to roll on the floor when moving system 10.

In one embodiment, translating component 36 includes a linear guide 40 suitable to control the translational motion along the sliding direction that is substantially parallel to main direction 20. Translating component 36 may include a carriage 42 suitable to slide along linear guide 40. In one embodiment, the carriage moves along the linear guide with the assistance of a motor. Any suitable mechanism may be used to move the gantry 22, either manually or mechanically/automatically.

In one embodiment, the radiological imaging system includes a rotation device (not shown) suitable to rotate gantry 22 about an axis of rotation that is substantially perpendicular to main direction 20 and, specifically, substantially perpendicular to the floor. The rotation device may include a first plate that is integrally attached to carriage 42. The rotation device may also include a second plate integrally attached to gantry 22. In addition, the rotation device may include a rotation component (not shown) that has pins, bearings, or other known mechanical elements suitable to permit the second plate, and thereby gantry 22, to rotate about the axis of rotation, in relation to the first plate, and therefore to the rest of radiological imaging system 12. The rotation device may also have a control lever or other mechanism, suitable to be held by an operator, to control the rotation of gantry 22 about the axis. A handle or any other type of grip may be used to control the rotation of gantry 22 about the axis.

In one embodiment, the rotation device and the control lever permit gantry 22 to be disposed in at least two configurations. One possible configuration is a working configuration in which gantry 22 is substantially perpendicular to main direction 20. Another possible configuration is a rest configuration in which gantry 22 is substantially parallel to main direction 20. In the rest configuration the bed may no longer be attached to the imaging system. The rotation device and control lever may also permit the gantry to be in a variety of other positions and angles relative to main direction 20. The robotic arm may also be put into a rest configuration in which the robot arm is not extended and allows the entire system to be transported more easily.

One example of an imaging system is disclosed in U.S. Pat. No. 10,016,171, the entirety of which is incorporated herein by reference, as if set forth fully herein. In one embodiment, detector 30 detects radiation when performing at least one of tomography, fluoroscopy, radiography, and multimodality and generates data signals based on the radiation received. Furthermore, in one embodiment, at least one detector includes at least one flat panel sensor and/or at least one linear sensor. In an example embodiment in which the at least one detector is a flat panel sensor, the flat panel sensor is selectably operable in at least a flat panel mode and a linear sensor mode obtained, for example, by activating one or more pixel rows that are, preferably, substantially perpendicular to the axis of the bore. In a further example embodiment herein, in the flat panel mode, the sensor performs at least one of fluoroscopy and tomography and, in the linear sensor mode, performs at least one of radiography and tomography. Other examples of an imaging system are disclosed in U.S. Pat. No. 9,510,793 and U.S. application Ser. Nos. 14/323,861; 14/800,659; and 14/821,227, each of which is incorporated herein by reference in its entirety, as if set forth fully herein. The system disclosed in this application may incorporate any of the imaging systems disclosed in these referenced applications, as robotic arm 14 and sensorized surgical guide 16 may be attached to a portion of any of these referenced imaging systems.

Robotic arm 14 and sensorized surgical guide 16 may be used with various other imaging devices or systems such as MRI devices. Robotic arm 14 and sensorized surgical guide 16 may be designed such that the robotic arm attaches to bed 18 or the imaging system for examination, and then may be detached from the bed or imaging system after the examination.

As shown in FIG. 1, robotic arm 14 includes base 50 and several arm segments 52 connected to one another. Arm segments 52 are able to rotate and move in relation to each other by way of a motor or individual motors and gears located at the junction between each arm segment. The base may be attached to radiological imaging system 12 or bed 18. The base of the robotic arm may be moved in any direction, both parallel and perpendicular to the main axis. In other embodiments, base 50 may be positioned independent of the radiological imaging system or the bed and be independently positioned near the area of interest. In this embodiment, the robotic arm may include wheels that allow movement in any direction to be in proper position adjacent to the patient. The wheels of the robotic arm in this embodiment may lock in place. The robotic arm may be positioned independently on the floor and not be connected to the imaging system or the bed. In yet another embodiment, base 50 of the robotic arm may be removably attached to the imaging system, the bed, or other object in the surgery room. The base may house a motor capable or moving one or more of the arm segments. The last arm segment holds sensorized surgical guide 16, which may be removably or permanently attached to the arm segment of robotic arm 14.

In one embodiment, robotic arm base 50 may be mounted on base 34 of the radiological imaging system. In this embodiment, the robotic arm base moves in the same translational direction of the gantry over the target and/or bed. The robotic arm may be a modular arm that may be removed from the gantry track or any other mounting point of the radiological imaging system, for ease of use, and mount and dismount from the radiological imaging system. According to one embodiment, the modular robotic arm may be mounted upon a mobile cart that is motorized (on treads, wheels, etc.) or manually driven by a user from one location to another location. According to another embodiment, the modular robotic arm is mounted directly to the gantry, at a fixed point or on an internal or external track that is separate from the gantry track, or to either end of the base platform of the radiological imaging system. In yet another embodiment, more than one modular robotic arm is mounted to the radiological imaging system. Each of the modular robotic arms may be equipped with a unique tool to perform a specific task.

In one embodiment, the robotic arm may incorporate six-degree-of-freedom force sensors, to be used to obtain controlled compliance in case of contact (voluntary or not) with the surgeon. This compliance may be obtained just along the intervention axis or along any other axis, depending on a pre-setting in control software. These compliances may be used to adapt the robotic arm position with respect to a cannula and the patient.

System 10 may also include a system computer or server that is in communication with radiological imaging system 12, robotic arm 14, and sensorized surgical guide 16. The system computer or server also may be in communication with a display and graphical user interface. In one embodiment, the system computer includes navigation software capable of referencing a position and orientation of an axis of intervention point and instructing robotic arm 14 to move sensorized surgical guide 16 to align with the axis of intervention point. Data from the sensorized surgical guide related to the translation and rotational movement of a surgical instrument positioned through the sensorized surgical guide may be sent to the system computer in order to monitor the movement of the surgical instrument within the body of the patient. Images from the radiological imaging system 12 may also be sent to the system computer and displayed, which may allow the surgeon to view the target area to be treated. Using the images from the radiological imaging system, the navigation software may allow the surgeon to find the best axis of intervention point. Any data from a patient monitoring or tracking device may also be sent to the system computer. The surgical instrument may also be marked or coated such that it is more visible using the radiological imaging system. In one embodiment, the surgical instrument is radio-opaque. In some embodiments, only certain instruments, with special markings or the like, may be recognized by sensorized surgical guide 16. In this way, the system may more precisely be calibrated to provide more accurate translation and rotation measurements, because the software that handles the measurements may recognize the particular instrument and load the related calibration table. This result may be obtained by using a coated texture (that the sensor on the surgical guide could recognize) or by an RFID or other embedded identification system.

Figure 13A:
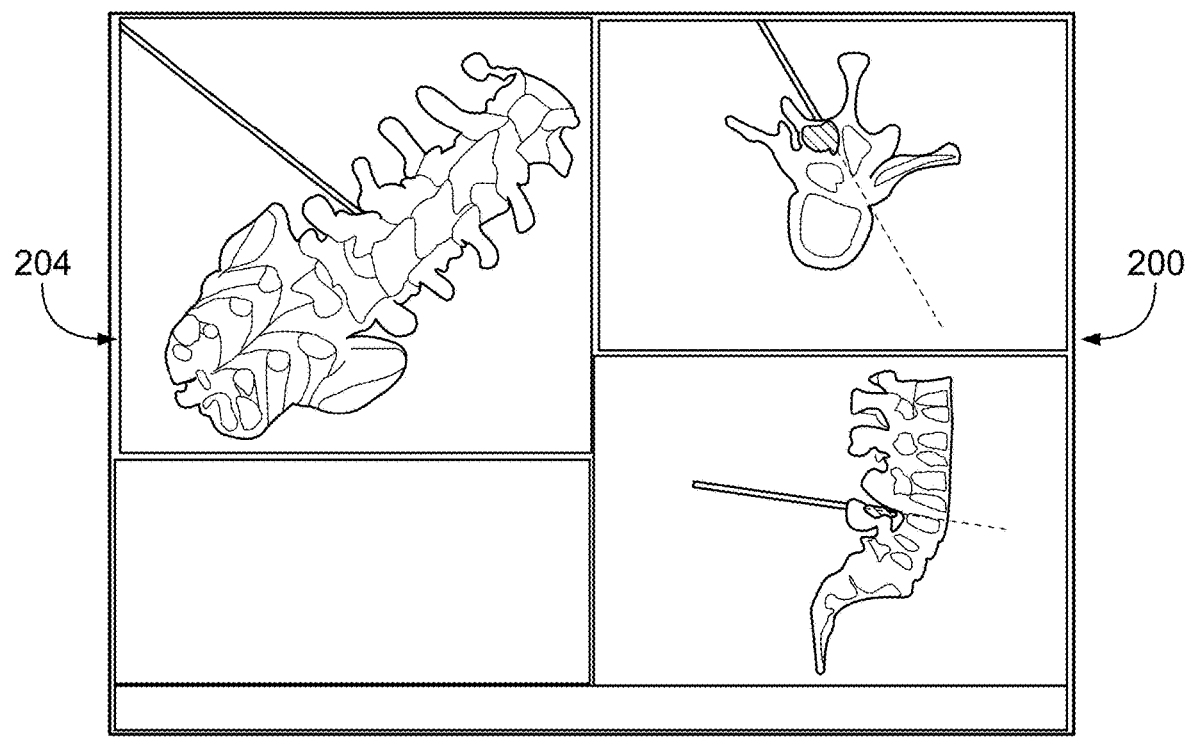
FIGS. 13A and 13B are exemplary screen shots from a display of a surgical system showing fluoroscopic images and indicators used by a surgeon during surgery, according to an embodiment of the present invention.
Figure 13B:
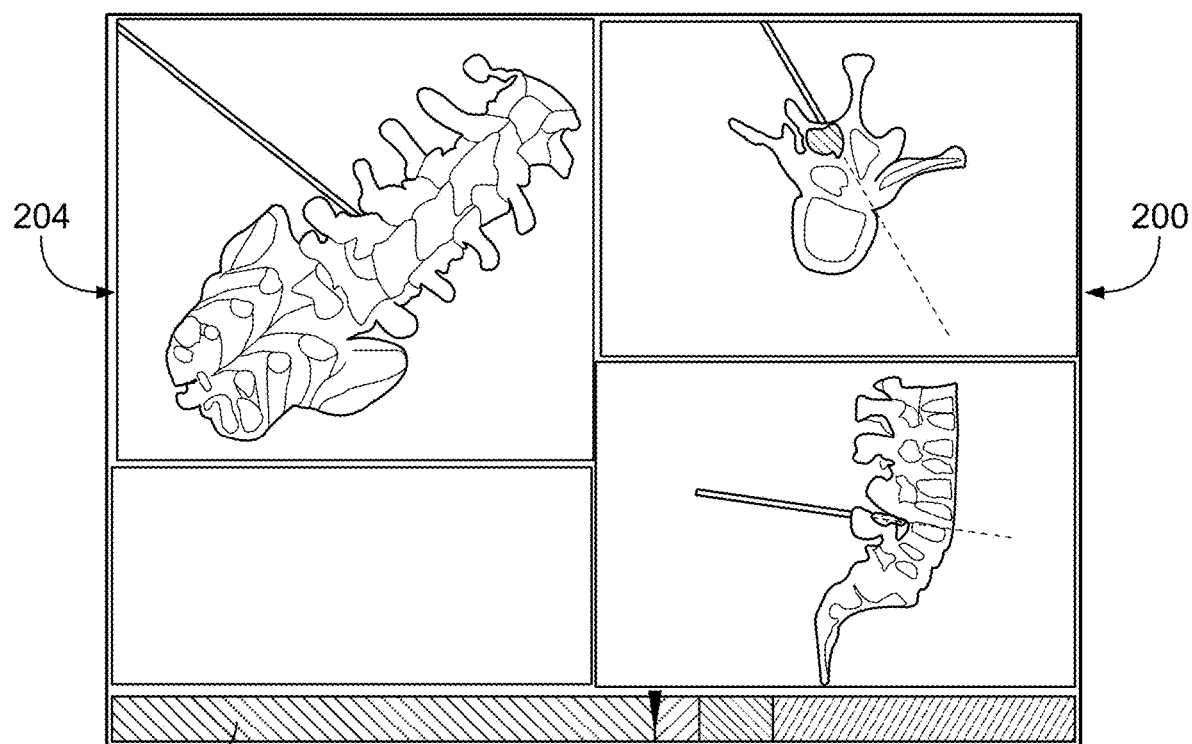

Embodiments of a display 200 associated with the system computer and navigation software are shown in FIGS. 13A and 13B. As shown in FIG. 13A, the system computer may show images 204 from radiological imaging system 12. Furthermore, the navigation software on the system computer may show the axis of intervention point and even determine or assist in determining the safest and most efficient axis of intervention point. As shown in FIG. 13B, the system computer also may show on display 200 a color-coded bar 202 indicating the depth of the surgical instrument in the body of the patient. Other indicia indicating the depth of the surgical instrument also may be shown on the display. The surgical team may select the images, information, or color-coded bars to show on the display.

Figure 3:
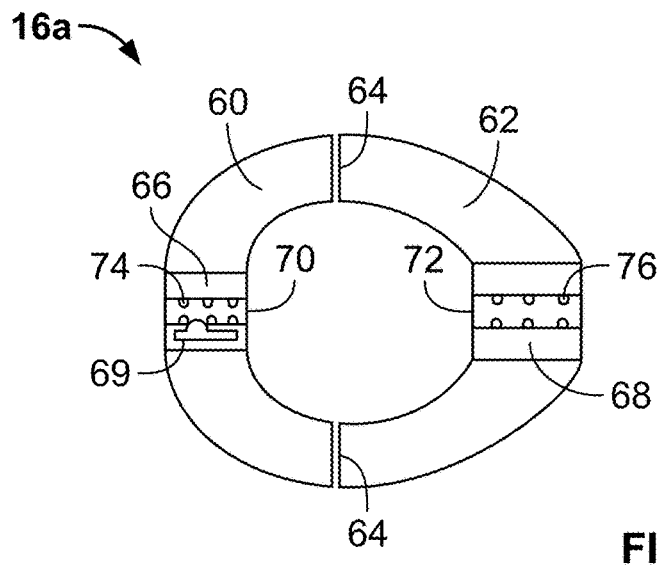
FIG. 3 shows an exemplary sensorized surgical guide having a hinged structure, according to an embodiment of the present invention.

One embodiment of sensorized surgical guide 16a is shown in FIG. 3. In this embodiment, the sensorized surgical guide includes a proximal or rotational section 60 attached to a distal or fixed section 62. Hinges 64 may attach the proximal section to the distal section. The hinges allow proximal section 60 to rotate up to 180 degrees with respect to the plane defined by distal section 62. In one embodiment, distal section 62 may be fixed or rigidly connected to the last arm segment of robotic arm 14. A proximal guide 66 is disposed on proximal section 60 and a distal guide 68 is disposed on distal section 62. The proximal and distal guides have through holes 70, 72 in alignment with one another. In one embodiment, the proximal and distal guides each include ball bearings 74 and 76. The ball bearings help translate a surgical instrument through the proximal and distal guides. Moreover, the ball bearings may be spring loaded to put pressure on any instrument being slid through the guides. In other embodiments, through holes 70 and 72 may be coated with a low friction material (like PET+PTFE, for pharma and alimentary uses) instead of using ball bearings. The diameters of through holes 70 and 72 may have different sizes. For instance, the inner diameter of distal through hole 72 may be equal to the outer diameter of a surgical instrument such as a cannula. The diameter of proximal through hole 70 may be equal to or slightly larger than the inner diameter of the cannula in order to accommodate surgical instruments that may be inserted through the cannula. In one embodiment, the diameter of through hole 70 may range from about 2 mm to about 15 mm.

As shown in FIG. 3, proximal guide 66 may include a surface reader 69 capable of measuring the translation of a surgical instrument. Surface reader 69 may also be used to measure the rotation of the surgical instrument. In one embodiment, the surface reader may be an Optical Navigation Chip. The surface reader may be similar to a sensor in a PC mouse. In other embodiments, surface reader 69 may include a camera that is disposed over a movable opaque surface and illuminated. In this embodiment, the surface movements of the surgical instrument are detected by surface reader 69 and X, Y quadrature digital signals may be outputted by the surface reader as a result of the movement. In certain embodiments, the Optical Navigation Chip may provide X, Y displacements on a serial line, and each time the Optical navigation Chip is read, the X, Y registers are reset. The reader is then able to accumulate the X, Y displacements and rescale them in order to make the expected translation/rotation measurement. As an example, the quadrature signals may be used as the equivalent of two incremental encoders and sent, with a specific interface between, to a computer operating navigation software, where those signals may be used for monitoring in real time the penetration of the surgical instrument in the body.

Figure 4:
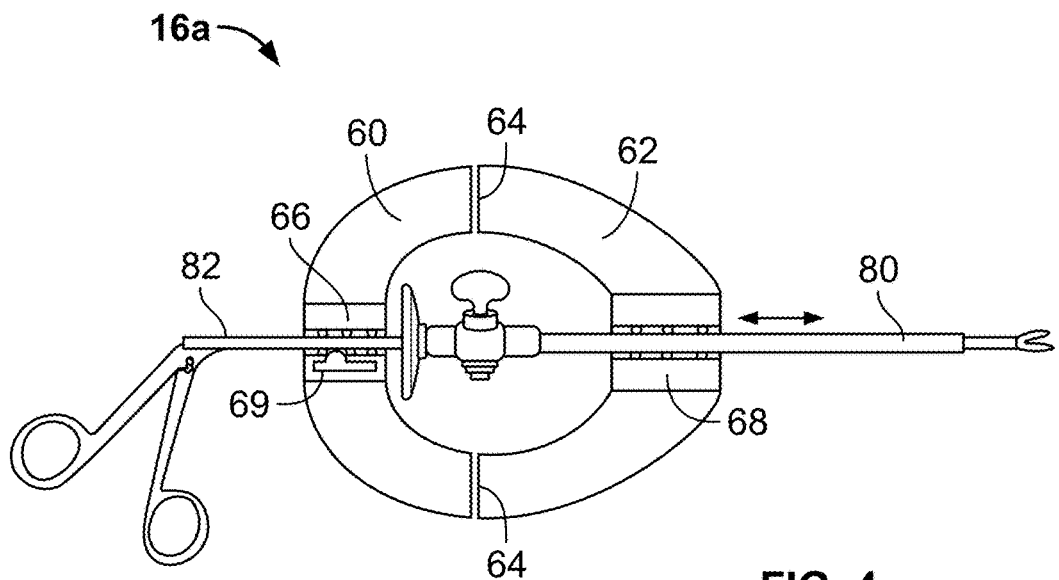
FIG. 4 shows the sensorized surgical guide of FIG. 3 in use with a cannula positioned in a distal guide and a surgical instrument positioned in a proximal guide and the cannula, according to an embodiment of the present invention.

By way of example only, and not by way of limitation, FIG. 4 shows one embodiment for using sensorized surgical guide 16a. In this example, the proximal section is rotated (not shown) in order to place a cannula 80 through the hole of distal guide 68. As stated above, the inner diameter of the distal guide should be sized such that the cannula is able to translate along the distal guide in a straight line without allowing the cannula to wobble or move in an angle that is not parallel to through hole 72. Once the cannula is in position, the proximal section is rotated and locked such that guides 66 and 68 are aligned with one another. An instrument, such as a gripper 82, may be slid through proximal guide 66 and into cannula 80. The working end of the gripper may exit the distal end of the cannula as shown in FIG. 4.

Figure 5:
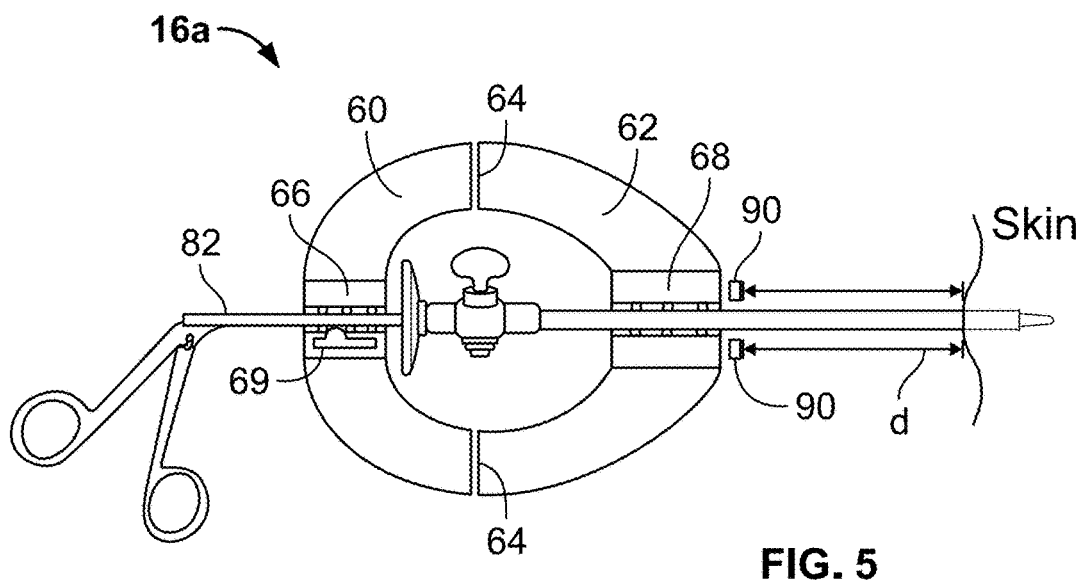
FIG. 5 shows an exemplary sensorized surgical guide including distance sensors disposed on the distal end of the sensor guide, according to an embodiment of the present invention.

In another embodiment, sensorized surgical guide 16a may include at least one, and preferably two, distance sensors 90 on the distal end of distal section 62 as shown in FIG. 5. The distance sensors are capable of sensing in real-time the distance between the sensorized surgical guide and the skin of the patient. In one embodiment, the distance sensors may be time-of-flight laser ranging sensors. When the distance between the sensors and the patient is less than a predetermined threshold, an alarm signal could be produced and sent to a controller of robotic arm 14 to activate a safety function. Although the threshold range may be set to any distance, in one embodiment, the threshold range may from about 3 mm to about 100 cm. If the threshold distance between the sensors and the patient is breached, the robotic arm may be programmed to move away from the patient along the intervention axis, the surgical instruments may be released from the sensorized surgical guide, or the robotic arm could disengage along the insertion point. These safety features could prevent a collision between the sensorized surgical guide 16a and the patient body in case the patient body is moved during the intervention.

Figure 6:
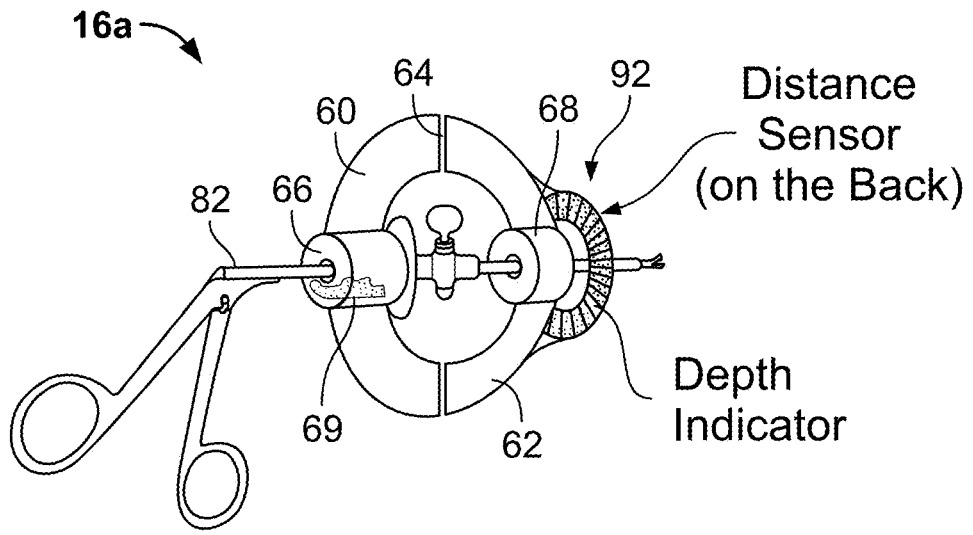
FIG. 6 shows another exemplary sensorized surgical guide including a depth indicator to alert a surgeon to the depth of a surgical instrument inside a patient, according to an embodiment of the present invention.

In another embodiment, the sensorized surgical guide 16a may include a bar display 92 as shown in FIG. 6. The bar display may include LED lights or other illuminators that indicate distance between the guide and the patient body or the depth of the surgical instrument inside the patient body based on color or a distance reader (e.g., a bar graph). In another embodiment, the bar display 92 may include a display indicating the distance and depth information as a numeric value. The same information indicated by the bar display may be shown on a monitor, but the display may not be in the surgeon's view. For this reason, it may be beneficial to include the bar display on sensorized surgical guide so that the information concerning the depth of the surgical instrument is in the surgeon's view when performing the operation. The depth indicator on the bar display may be driven by the system computer running the navigation software.

Figure 7:
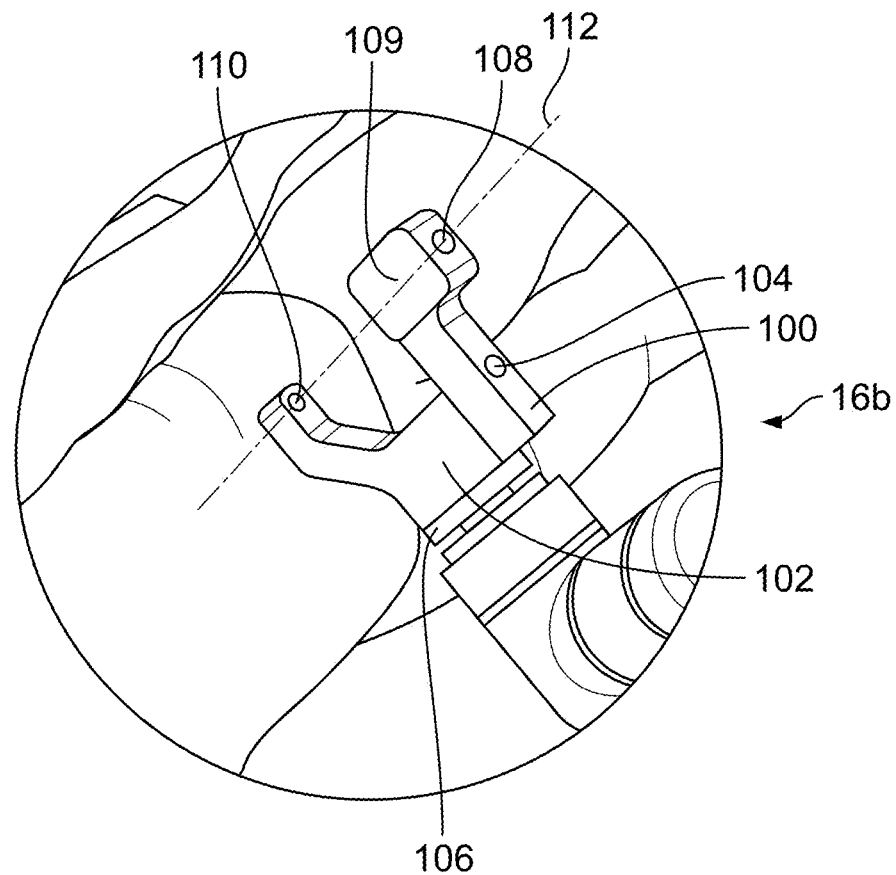
FIG. 7 shows another exemplary sensorized surgical guide having a generally U-shape attached to a robotic arm, according to an embodiment of the present invention.

Another embodiment of a sensorized surgical guide 16b is shown in FIG. 7. In this embodiment, sensorized surgical guide 16b is generally U-shaped and includes a proximal or rotational section 100 attached to a distal or fixed section 102. A pivot 104, such as a pin or a bolt, may attach proximal section 100 to distal section 102. The pivot allows proximal section 100 to rotate up to 360 degrees or 90 degrees in any direction around the axis of the pivot. As shown in FIG. 7, distal section 102 may be connected to end portion 106 on the last arm segment of robotic arm 14. End portion 106 or the last segment of the robotic arm may be able to rotate up to 360 degrees around the axis formed by the last arm segment of the robotic arm, and the end portion may be able to tilt in any direction to adjust the location of the sensorized surgical guide. A proximal guide 108 is disposed on proximal section 100 and a distal guide 110 is disposed on distal section 102. The proximal and distal guides each have a through hole in alignment with one another along an axis of intervention point 112. Proximal guide 108 and distal guide 110 may be the same as the proximal and distal guides described above with respect to sensorized surgical guide 16a. In this way, the proximal and distal guides may each include ball bearings that help translate a surgical instrument through the proximal and distal guides along the axis of intervention point 112. Moreover, the ball bearings may be spring loaded to put pressure on any instrument being slid through the guides. The diameters of the through holes on the proximal and distal guides may have different sizes. For instance, the inner diameter of the through hole on the distal section may be equal to the outer diameter of a surgical instrument such as a cannula. The through hole of the proximal section may be equal to or slightly larger than the inner diameter of the cannula in order to accommodate surgical instruments that may be inserted through the cannula. In one embodiment, the diameter of the through hole may range from about 2 mm to about 15 mm.

Furthermore, proximal guide 108 may include a surface reader or a displacement sensor 109 capable of measuring the translation of a surgical instrument. As discussed above, the surface reader or displacement sensor also may be used to measure the rotation of the surgical instrument. The various types of surface readers described above with respect to surface reader 69 may also be used with sensorized surgical guide 16b.

In one embodiment, the connection between distal section 102 and end portion 106 of the robotic arm may be a releasable connection, such as an electro-magnetic connection. This connection may also be pneumatic, hydraulic, or the like. In this embodiment, the connection may be controlled by the system computer or may manually be released. In use, if there were an issue, the system computer or surgeon could release the connection between distal section 102 and end portion 106 of the robotic arm to abort the robot-assisted holding of the cannula or other surgical instrument. In other embodiments, there may be a releasable connection located anywhere under proximal guide 108 and a separate releasable connection located anywhere under distal guide 110. As above, the releasable connection may be an electro-magnetic connection, pneumatic, hydraulic, or the like. Similarly, the releasable connection(s) in this embodiment may be controlled by the system computer or manually released by the surgeon in case aborting the robot-assisted holding of the cannula or other surgical instrument is necessary.

In yet another embodiment, proximal guide 108 and/or distal guide 110 may include a locking mechanism to prevent the movement of a surgical instrument or cannula, respectively. The locking mechanism may be controlled by the system computer or may be manually activated by the surgeon. In certain embodiments, the locking mechanism may be a mechanical spring-based device or an electro-magnetic coil-based device. In use, if sensors determine that the patient body has moved or the sensorized surgical guide or robotic arm breaches a threshold distance to the patient body, the system computer may activate the locking mechanism and prevent further translation of the cannula or surgical instrument.

By way of example only, in use, proximal section 100 is rotated approximately 90 degrees in order to place a cannula through the hole of distal guide 110. As stated above, the inner diameter of the distal guide should be sized such that the cannula is able to translate along the distal guide in a straight line without allowing the cannula to wobble or move in an angle that is not parallel to the axis of intervention point 112. Once the cannula is in position, proximal section 100 is rotated back into its original working configuration and locked such that guides 108 and 110 are aligned with one another. An instrument may be slid through proximal guide 108 and into cannula 80 held within distal guide 110. The working end of the surgical instrument may exit the distal end of the cannula.

By way of example only, and not by way of limitation, a method of using system 10 will be described using sensorized surgical guide 16b. The sensorized surgical guide 16a, however, could be used in place of sensorized surgical guide 16b. In one embodiment, a surgical team diagnoses a patient and identifies a defect or target area, such as a tumor, that needs to be removed from the body. The surgical team plans the needed surgery including the point and angle of intervention into the body of the patient. Radiological imaging system 12 may be used to visualize a portion of the patient's body in order to plan the surgery and determine the intervention point and angle. In this example, the surgical team plans to remove a tumor from the patient.

Figure 8:
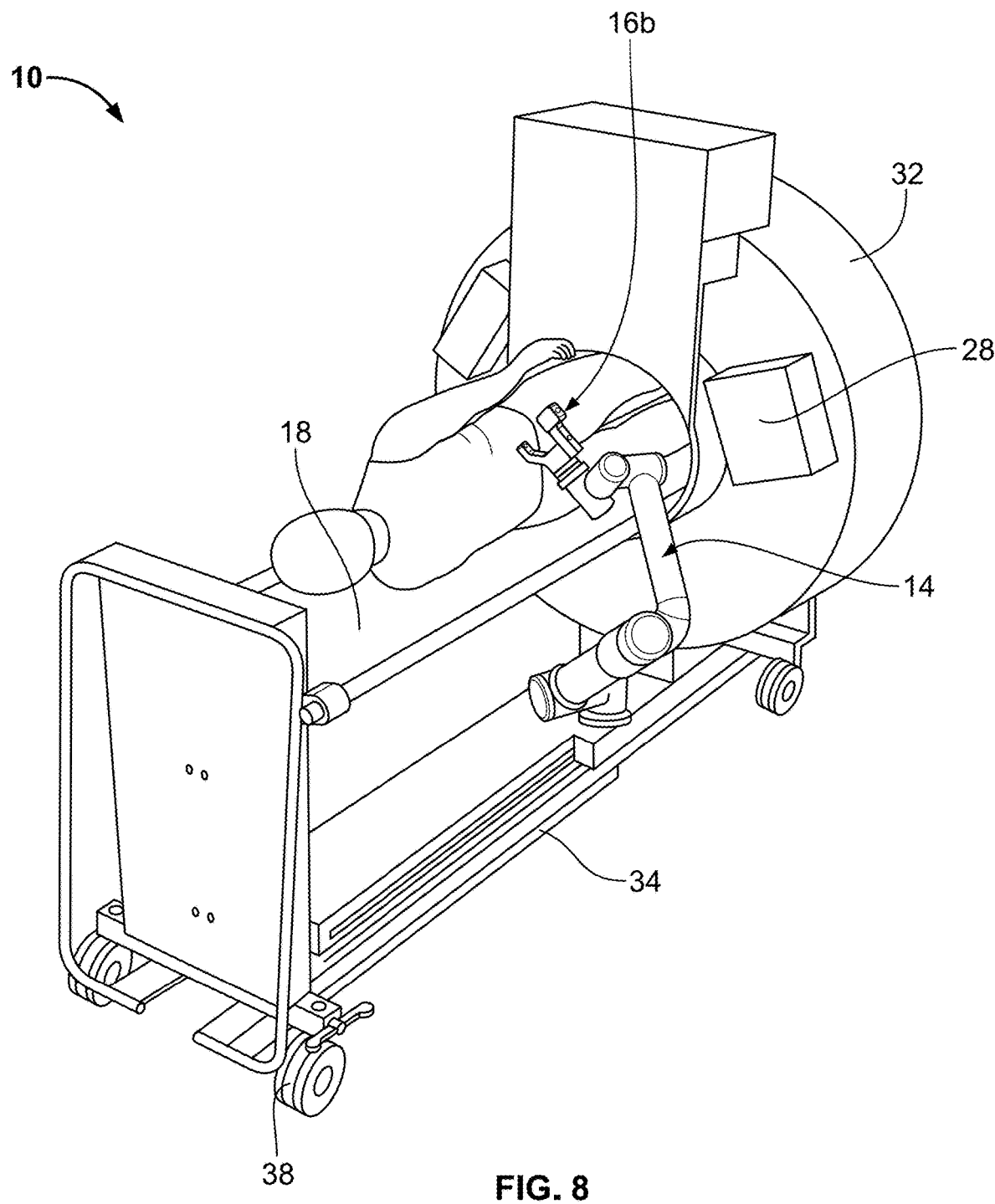
FIGS. 8-12 show exemplary steps to perform a surgical procedure using a surgical system including a radiological imaging system and a sensorized surgical guide attached to a robotic arm, according to an embodiment of the present invention.

As one of the initial steps, the patient is placed on bed 18 and the position of the body is scanned or otherwise determined and stored in the system computer. The body of the patient may be strapped down or otherwise held in place to prevent movement on bed 18. In one embodiment, system 10 may constantly monitor the position of the body or at least the target area on the patient. This may be done by reading sensors attached to the body of the patient, such as infrared (IR) sensors or other sensors that may be monitored by the navigation software system. Other technologies that monitor distance and location, such as a stereo IR camera and the like may be used. In addition to knowing the position of the body or at least the target area, the surgical team enters the intervention point and angle through the user interface of the system computer. In one embodiment, the system computer and navigation software may determine the axis of intervention point. The navigation software running on the system computer supplies the intervention point, angle, and direction (axis) of intervention to robotic arm 14, which moves to place sensorized surgical guide 16b (or 16a) along the axis of intervention point and at a certain distance from the patient body as shown in FIGS. 7 and 8.

Figure 9:
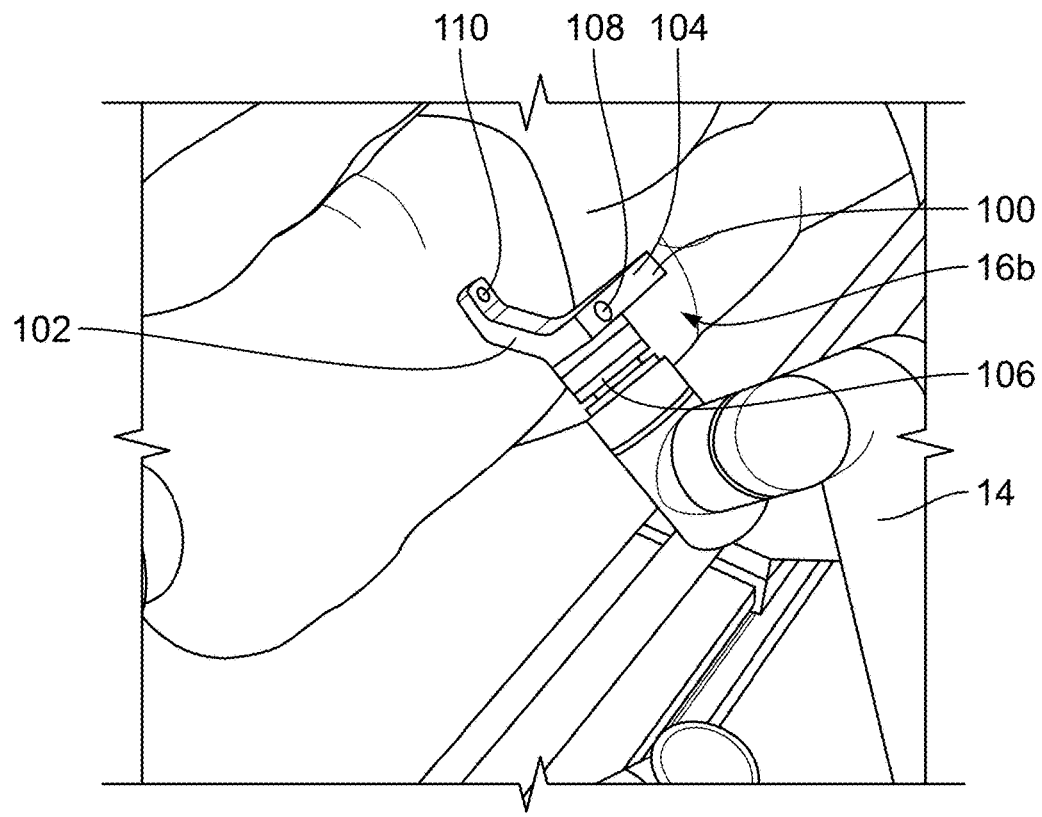
Figure 10:
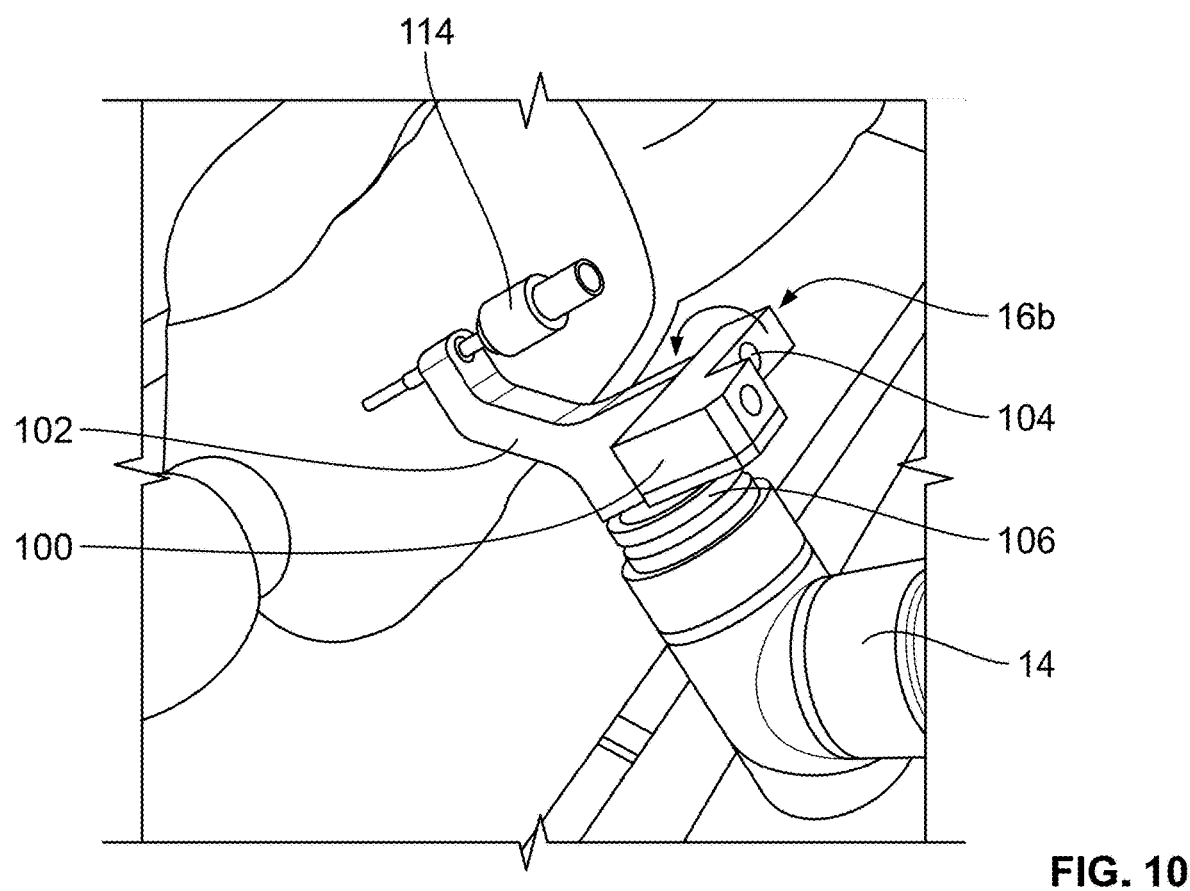
Figure 11:
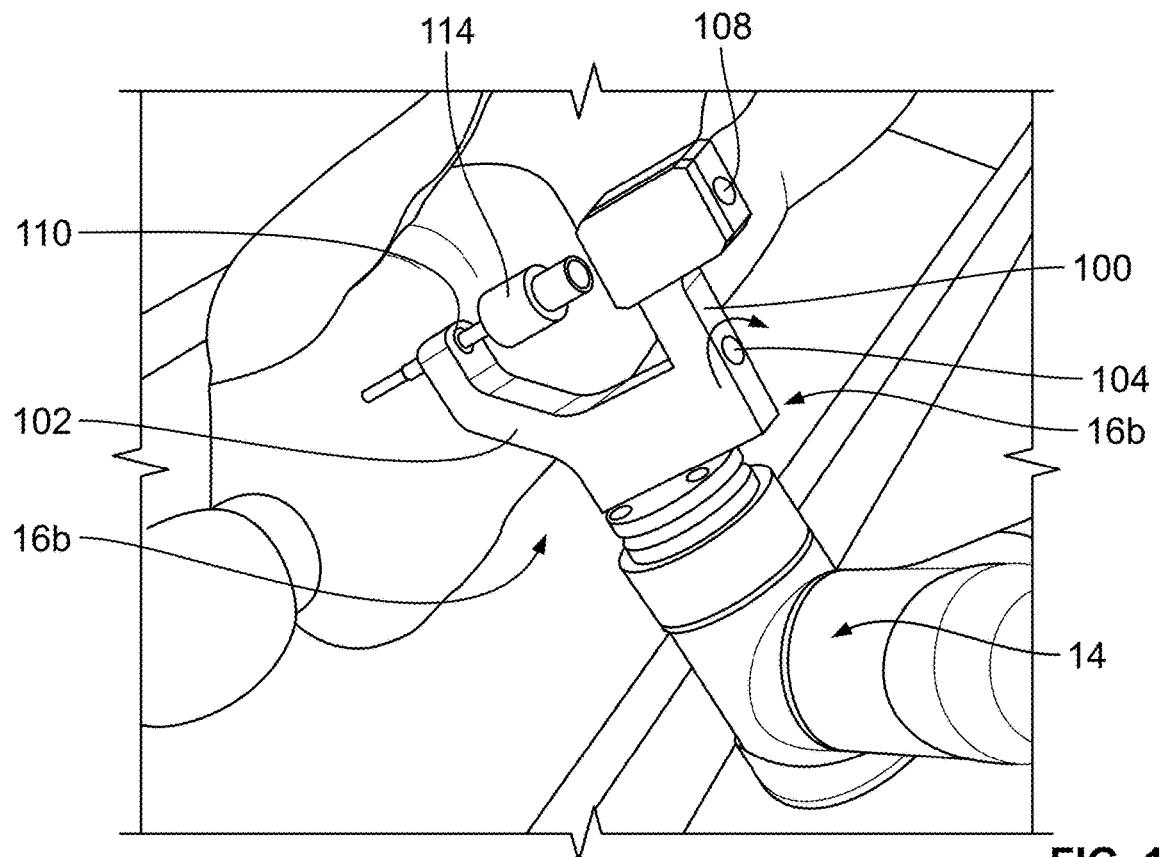
Figure 12:
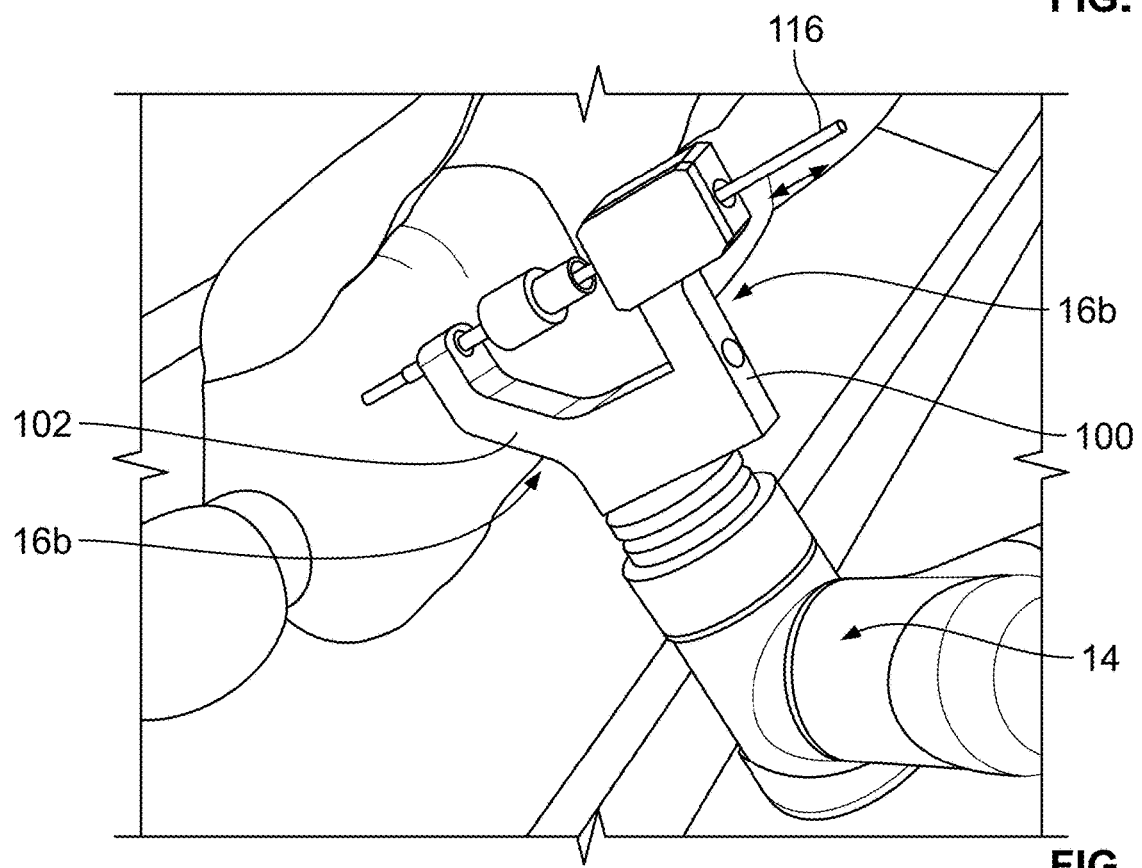

With sensorized surgical guide 16b in proper alignment with respect to the target area of the patient, the surgeon may open proximal section 100 of the sensorized surgical guide as shown in FIG. 9. Next the surgeon may insert a trocar and cannula 114, in one example, through distal guide 110 as shown in FIG. 10. The physician may then insert the trocar into the body of the patient as robotic arm 14 holds sensorized surgical guide 16b in position, which allows the surgeon to move the trocar in the insertion point direction only. Once the trocar has pierced the body and the cannula is sufficiently positioned within the body, the surgeon removes the cutting portion of the trocar, leaving in site the cannula. The surgeon may then close proximal section 100 of sensorized surgical guide 16b as shown in FIG. 11. With proximal guide 108 in line with axis of intervention point 112, the surgeon may insert a surgical instrument 116 through proximal guide 108 and into cannula 114 as shown in FIG. 12 to perform the surgical procedure.

The surgical procedure may be continually assessed to monitor the location of the surgical instrument with respect to the target area and other structures (veins, arteries, organs, etc.) in the body. In one embodiment, displacement sensor 109 of sensorized surgical guide 16b reads the surgical instrument's penetration depth and sends this information to the navigation software on the system computer. The navigation software may display the surgical instrument's penetration depth on display 200 using a color-coded bar 202 or other visual stimulus. In one embodiment, a 2-D fluoroscopy image(s) 204 may be shown on the display to visually monitor the location of the surgical image as shown in FIGS. 13A and 13B. The surgeon may use and take a fluoroscopy image at any point during the surgical procedure, and, in other embodiments, the fluoroscopy image may continuously be taken during the surgical procedure so the entire procedure may be followed on the display. Other information useful to the surgeon may also be shown on the display. Once the surgical procedure is complete, the surgical instrument and cannula are removed from the patient, and robotic arm 14 may be removed from system 10 or placed in a non-working configuration that allows greater access to the patient and allows the patient to be removed from imaging system 12.

Figure 14:
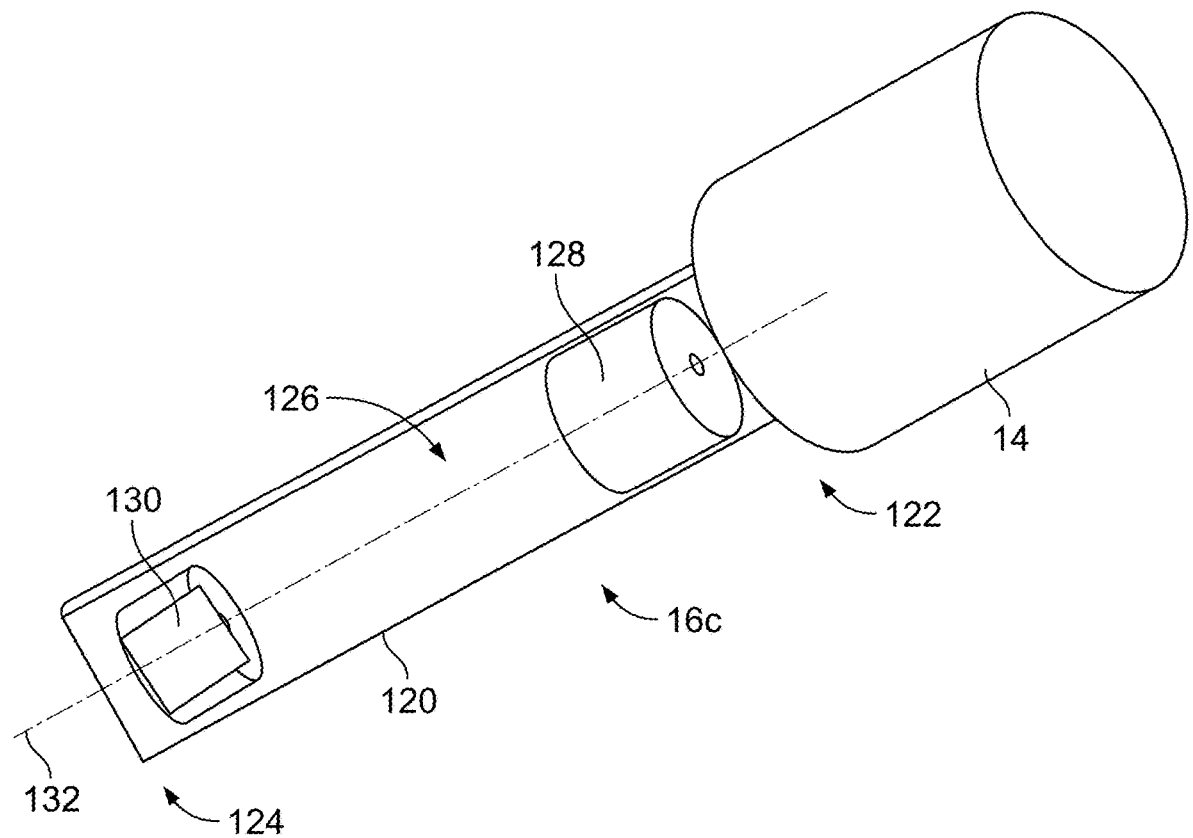
FIG. 14 shows another exemplary embodiment of a sensorized surgical guide attached to a robotic arm.

Yet another embodiment of a sensorized surgical guide 16c is shown in FIG. 14. In this embodiment, sensorized surgical guide 16c includes a holder arm 120 having a proximal end 122 and a distal end 124, with proximal end 122 attached to the last arm segment of the robotic arm. As shown in FIG. 14, holder arm 120 is generally tubular shaped and includes a window 126. A proximal guide 128 is disposed near proximal end 122 and may be movable from within holder arm 120. There also is a distal guide 130 disposed near distal end 124. The proximal and distal guides each have a through hole in alignment with one another along an axis of intervention point 132. The proximal guide 108 and distal guide 110 may be similar to the proximal and distal guides described above with respect to the sensorized surgical guide 16a. In this way, the proximal and distal guides may each include ball bearings that help translate a surgical instrument through the proximal and distal guides along the axis of intervention point 132. Moreover, the ball bearings may be spring loaded to put pressure on any instrument being slid through the guides. The diameters of the through holes on the proximal and distal guides may have different sizes. For instance, the inner diameter of the through hole on distal guide 130 may be equal to the outer diameter of a surgical instrument such as a cannula. The through hole of the proximal guide may be equal to or slightly larger than the inner diameter of the cannula in order to accommodate surgical instruments that may be inserted through the cannula.

Furthermore, proximal guide 128 may include a surface reader capable of measuring the translation of a surgical instrument. As discussed above, the surface reader also may be used to measure the rotation of the surgical instrument. The various types of surface readers described above with respect to surface reader 69 may also be used with sensorized surgical guide 16b.

By way of example only, a method using system 10 including sensorized surgical guide 16c will be described now. As one of the initial steps, the patient is placed on bed 18 and the position of the body is scanned or otherwise determined and stored in the system computer. The body of the patient may be strapped down or otherwise held in place to prevent movement on bed 18. In one embodiment, system 10 may constantly monitor the position of the body or at least the target area on the patient. This may be done by reading sensors attached to the body of the patient. Other technologies that monitor distance and location, such as cameras (e.g., Lidar), lasers, and the like, may be used. In addition to knowing the position of the body or at least the target area, the surgical team enters the intervention point and angle using the user interface of the system computer. The navigation software running on the system computer supplies the intervention point, angle and direction (axis) of intervention to robotic arm 14, which moves to place sensorized surgical guide 16c along the axis of intervention point 132.

Figure 15:
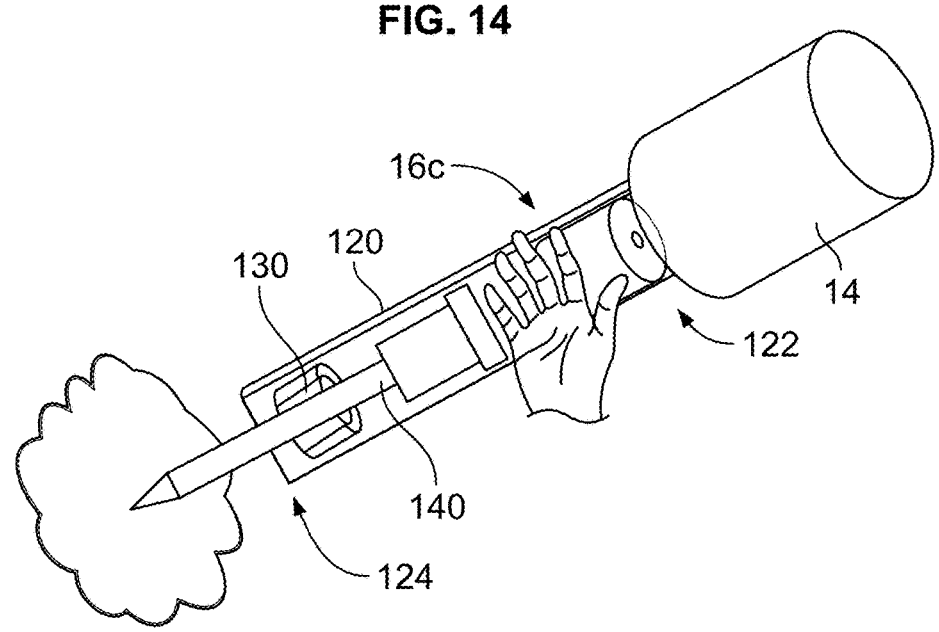
FIGS. 15-18 show exemplary steps to perform a surgical procedure using a surgical system including the sensorized surgical guide shown in FIG. 14, according to an embodiment of the present invention.
Figure 16:
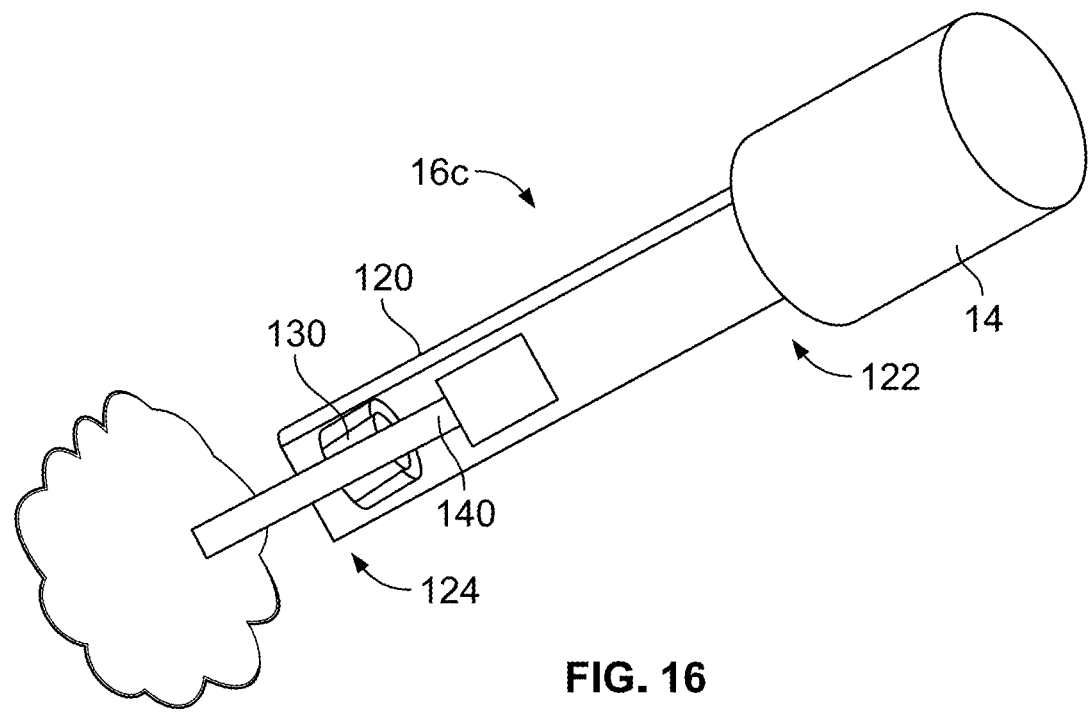
Figure 17:
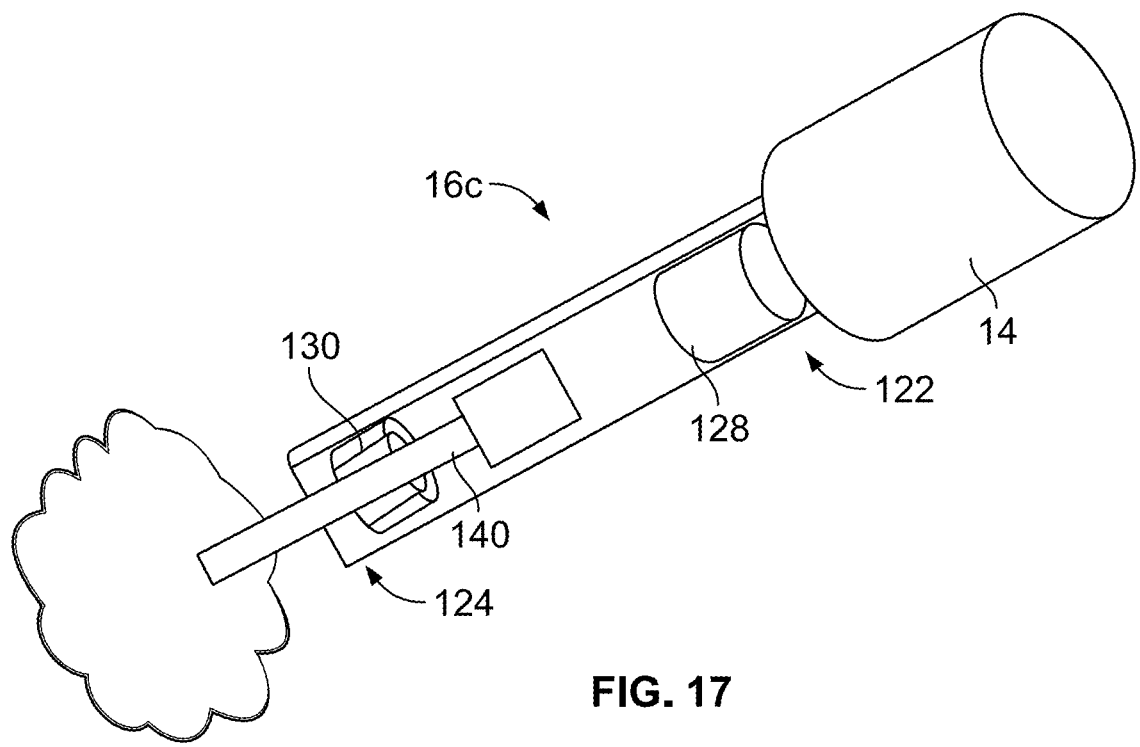

With sensorized surgical guide 16c in proper alignment with respect to the target area of the patient, the surgeon may insert a trocar and cannula 140 through window 126 and into holder arm 120, where the cannula is fed into and through the canal of distal guide 130 as shown in FIG. 15. The physician may then insert the trocar into the body of the patient as robotic arm 14 holds sensorized surgical guide 16c in position, which allows the surgeon to move the trocar in the insertion point direction only. Once the trocar has pierced the body and the cannula is sufficiently positioned within the body, the surgeon removes the cutting portion of the trocar, leaving in site the cannula as shown in FIG. 16. Once the cannula is in position, proximal guide 128 may be moved within holder arm 120 and secured into position near proximal end 122 as shown in FIG. 17. Proximal guide 128 may be secured within a cutout portion of the holder arm or, in other embodiments, proximal guide 128 may be moved into and out of the holder arm by using polished pins and rack and pinion gears.

Figure 18:
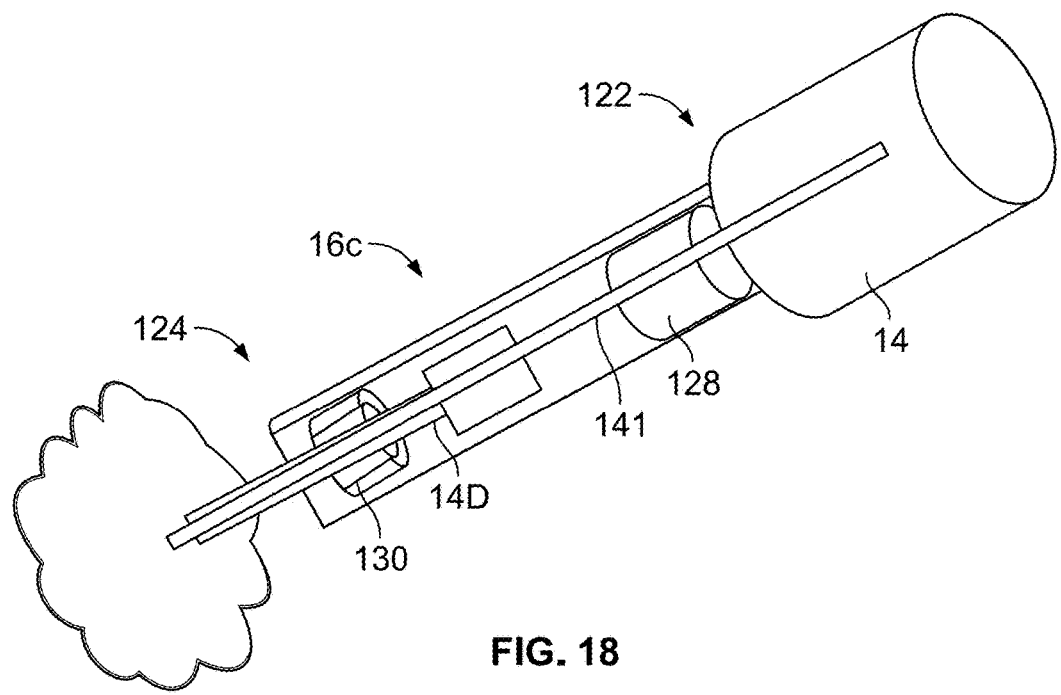

A surgical instrument 141 may then be slid through the canal of proximal guide 128 and into cannula 140 held within distal guide 130. The working end of the surgical instrument may exit the distal end of the cannula to perform the surgical procedure as shown in FIG. 18.

Figure 19:
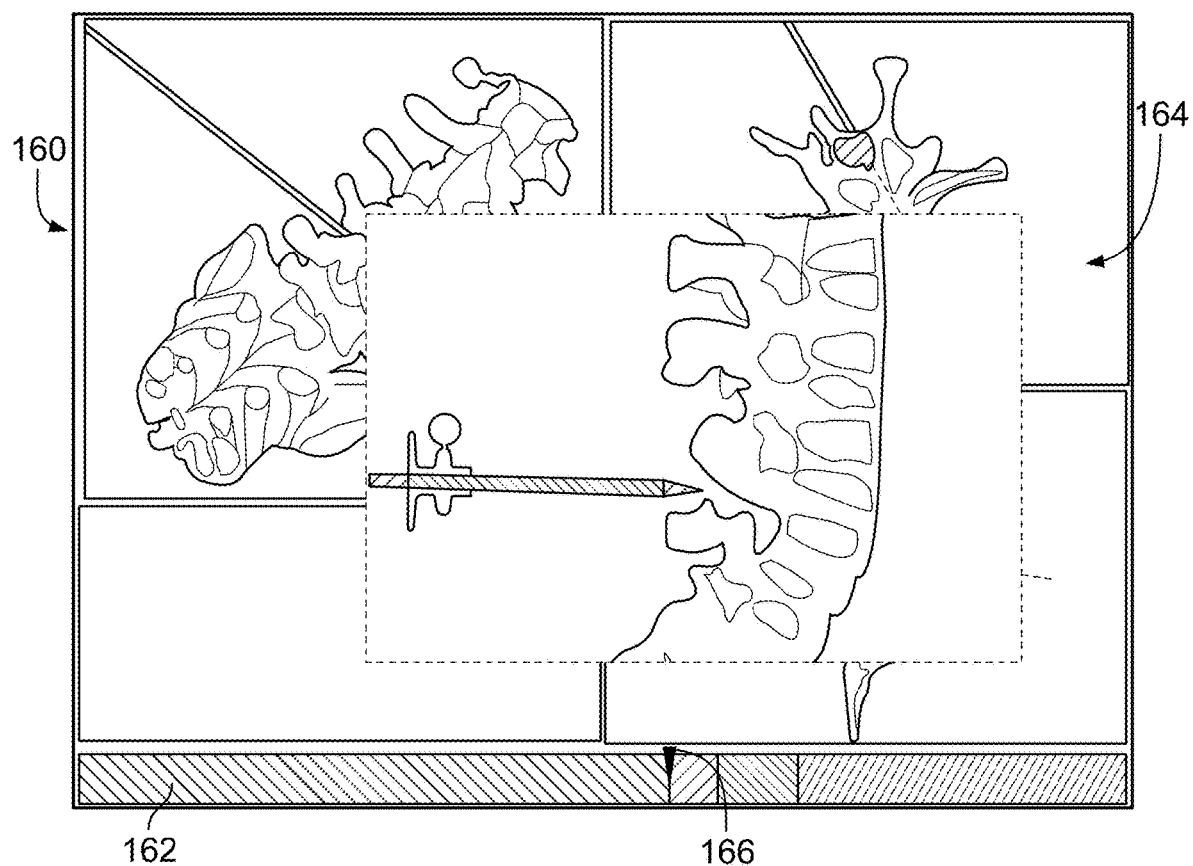
FIG. 19 is an exemplary screen shot from a display of a surgical system showing a fluoroscopic image and a colored bar code indicating the distance between the surgical instrument and the target area, according to an embodiment of the present invention.

The surgical procedure may be continually assessed to monitor the location of the surgical instrument with respect to the target area and other structures (veins, arteries, organs, etc.) in the body. In one embodiment, the surface reader in proximal sensor 128 of sensorized surgical guide 16c reads the surgical instrument's penetration depth and sends this information to the navigation software on the system computer. The navigation software may display the surgical instrument's penetration depth on a display 160 using a color-coded bar 162 or other visual stimulus. In this embodiment, the color-coded bar shows the distance to the target area, using green, orange, and red to tell the surgeon to advance (green), slow down (yellow), and stop (red) progression. A pointer 166 may be shown on the display to indicate the current position of the distal end of the surgical instrument. Audio and tactile stimuli may also be used to provide feedback to the surgeon when advancing the surgical instrument. Also, a 2-D fluoroscopy image(s) 164 may be shown on the display to visually monitor the location of the surgical instrument as shown in FIG. 19. The surgeon may use and take a fluoroscopy image at any point during the surgical procedure, and, in other embodiments, the fluoroscopy image may continuously be taken during the surgical procedure so the entire procedure may be followed on the display. Other information useful to the surgeon may also be shown on the display. Once the surgical procedure is complete, the surgical instrument and cannula are removed from the patient, and robotic arm 14 may be removed from system 10 or placed in a non-working configuration that allows greater access to the patient and allows the patient to be removed from imaging system 12.

Figure 20:
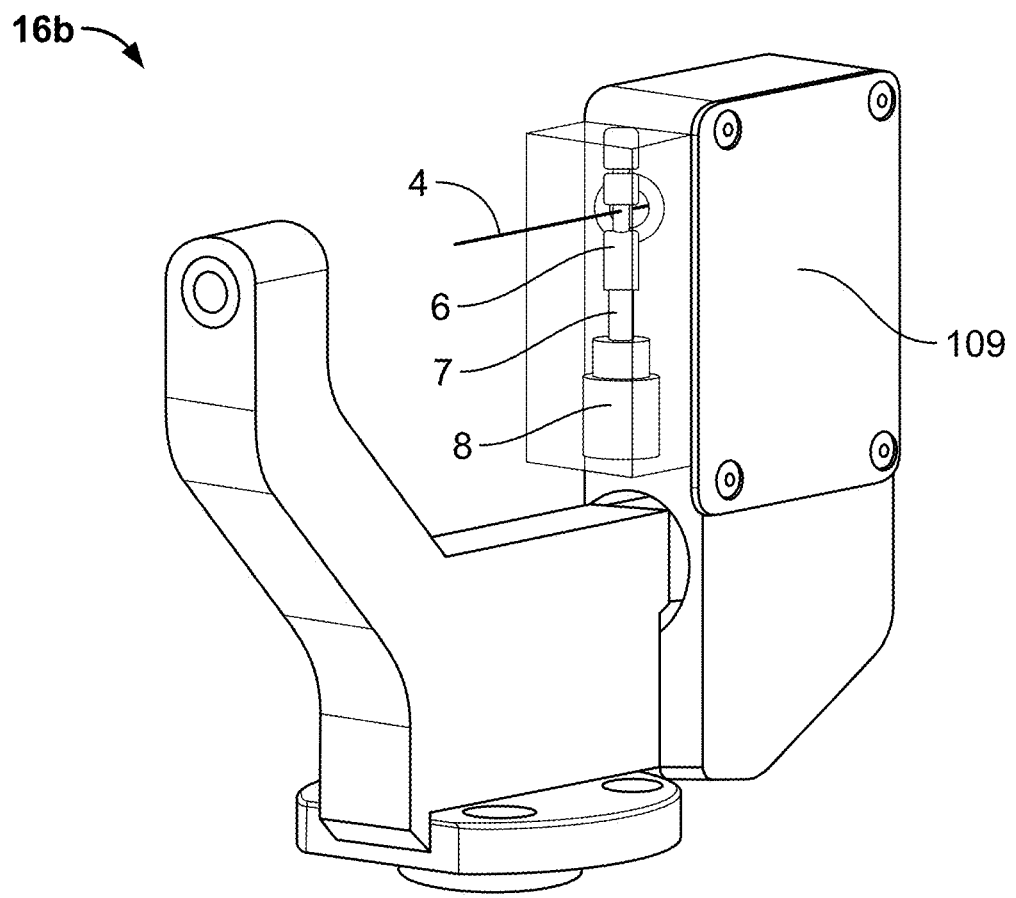
FIG. 20 is a schematic diagram of the sensorized surgical guide depicted in FIG. 7, according to an embodiment of the present invention.

The sensorized surgical guide may also control the use of surgical instruments during surgery. More specifically, the surface reader on the sensorized surgical guide that measures the translation and rotation of the inserted surgical instrument may also read markings or patterns on the surface of the surgical instrument itself. If the markings or patterns on the surgical instrument indicate that the instrument comes from an authorized source or is of an authorized type, a shutter assembly allows the surgical instrument to be used with the sensorized surgical guide Reference is now made to FIG. 20, which is a schematic diagram of sensorized surgical guide 16b, according to an embodiment of the present invention. Sensorized surgical guide 16b includes surface reader 109, piston 6, spring 7, and solenoid 8. In addition to surface reader 109 including a technology similar to that used in a PC mouse sensor, as described above, surface reader 109 may be a small video camera that detects the movement (e.g., translation and rotation) of a surface. This video camera may grab images of the surface at a certain frame rate, and, using software, the surface reader may process those images in order to understand the relative movement of the surface. The same image set may be also used to detect a pattern printed on the surface, and the software may generate a signal when the detected pattern matches a pre-loaded, authorized reference pattern. (It is also possible to mix the two features (pattern recognition+translation & rotation) or have more than one reader or camera (one for pattern recognition+one for translation & rotation.)

Figure 21A:
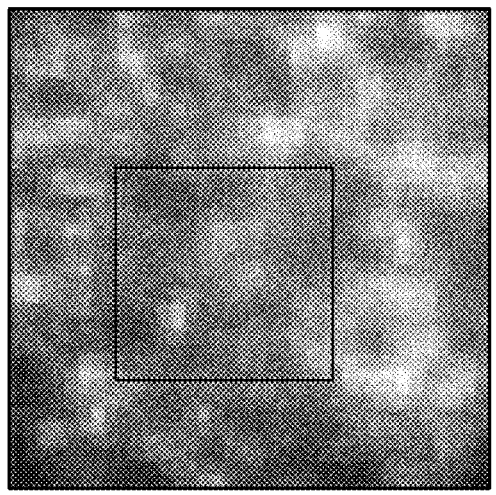
FIGS. 21A and 21B are exemplary pictures showing what the surface reader of a sensorized surgical guide sees, according to an embodiment of the present invention.
Figure 21B:
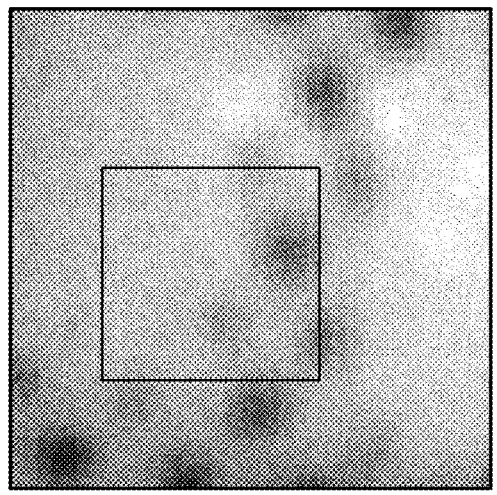

FIGS. 21A and 21B are exemplary pictures showing what the surface reader of sensorized surgical guide 16b may see, according to an embodiment of the present invention. FIG. 21A shows a normal surface; FIG. 21B shows an example of a patterned surface.

The generated signal when the pattern is detected may be used to command a shutter assembly made up of piston 6, spring 7, and solenoid 8. The shutter assembly may be an electro-mechanical device that is placed so as to obstruct, when commanded, surgical instrument path 4 (shown in FIG. 20). The obstruction may be partial or complete, depending on the embodiment of the shutter. In one embodiment, the obstruction may be realized using solenoid 8 and a plunger 9 (shown in FIGS. 22, 23A, and 23B). FIG. 22 shows that when solenoid 8 is energized, plunger 9 may be pulled within the solenoid, opening surgical instrument path 4.

The linear movement of plunger 9 may move piston 6, which, when solenoid 8 is de-energized, partially obstructs surgical instrument path 4. This position may be held using spring 7. When solenoid 8 is energized, plunger 9 is pulled within solenoid 8 and places piston 6 in a position such that surgical instrument path 4 is free. The field produced by solenoid 8 on plunger 9 should be capable of overcoming the resistance of spring 7. FIGS. 23A and 23B are schematic diagrams showing the de-energized and energized states, respectively, for this embodiment of the shutter assembly of sensorized surgical guide 16b.

Other shutter assemblies may be used in addition to or instead of the shutter assembly described above. The shutter may have an optional coating such as silicone to avoid potential instrument damage. One embodiment of a shutter may comprise an iris mechanism, e.g., a camera shutter that collapses circumferentially. Another embodiment of a shutter may comprise an inflatable or deflatable donut that closes the opening of the surgical path.

Figure 24:
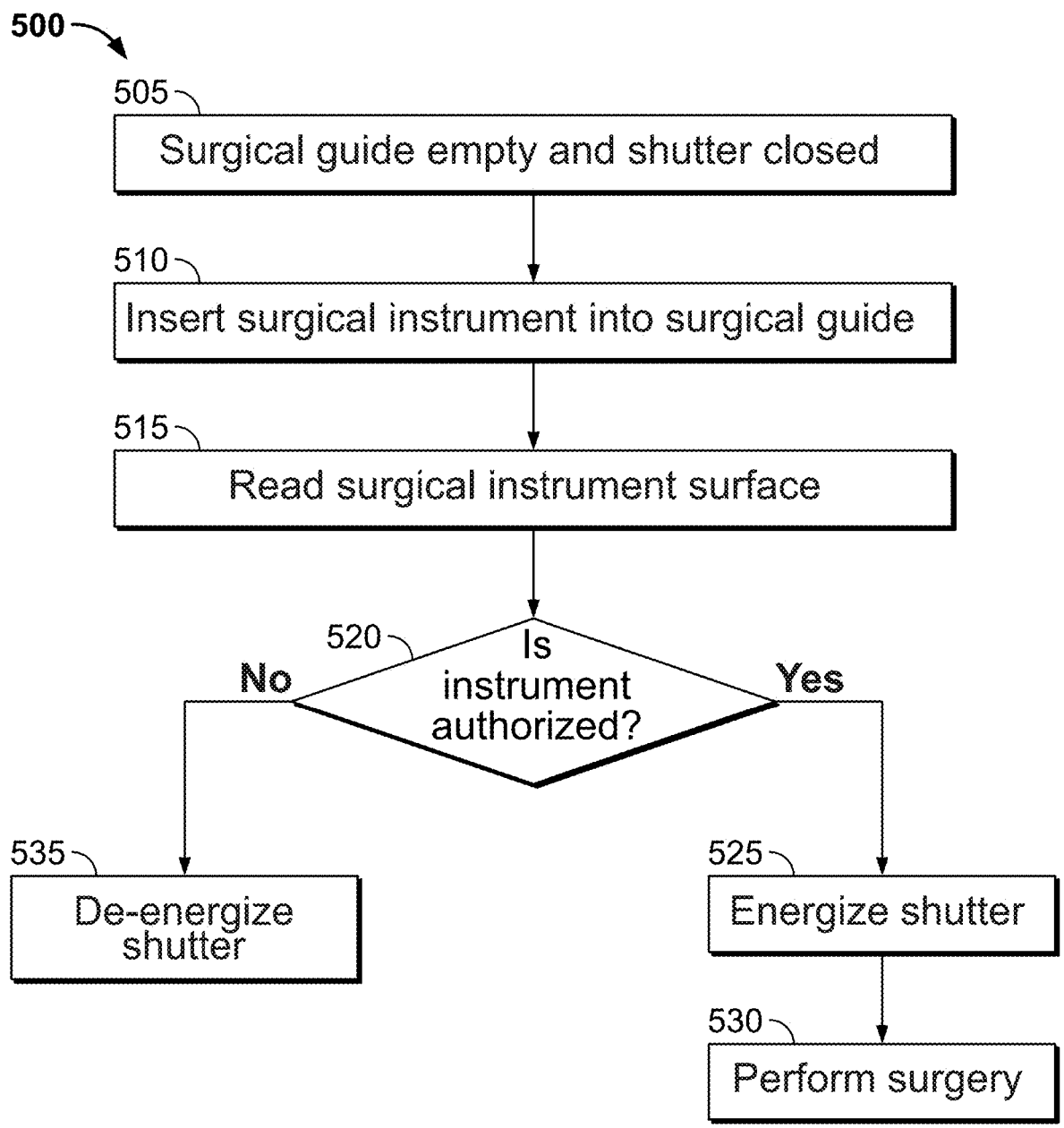
FIG. 24 is a flowchart of a process that controls the use of a surgical instrument during surgery, according to an embodiment of the present invention.

Reference is now made to FIG. 24, which shows a flowchart 500 of a process that controls the use of a surgical instrument during surgery, according to an embodiment of the present invention. In operation 505, sensorized surgical guide 16b is empty and the shutter is closed, i.e., it blocks passage of a surgical instrument. In operation 510, a surgical instrument may be inserted into sensorized surgical guide 16b by a person or by a robot, or a combination of both. In operation 515, the surface of the surgical instrument is read. In operation 520, the process asks whether the surgical instrument is authorized, which occurs if there are pre-authorized markings or a pre-authorized pattern on the surgical instrument. If the surgical instrument is authorized, in operation 525 the shutter may be energized, thus unblocking the surgical instrument path. In operation 530, surgery may then be performed. On the other hand, if the surgical instrument is not authorized, in operation 535 the shutter remains de-energized, and the surgical instrument path remains obstructed, thus not allowing surgery using sensorized surgical guide 16b. In another embodiment, a warning light or sound may be activated alerting the surgeon of the attempt to use an unauthorized instrument. Or a message may be displayed on a system monitor with such a warning or alert.

Besides the operations shown in FIG. 24 and their description in the other figures, other operations or series of operations are contemplated to control the use of surgical instruments during surgery. For example, each of the other sensorized surgical guides described above, 16, 16a, and 16c may include a surface reader capable of reading and identifying markings or patterns on a surgical instrument in addition to measuring translation and rotation of such instrument. The shutter assembly may be modified in order to fit within the confines of the specific surgical guide used.

The authorizing pattern may be cross-hatch marks, surface roughening, arrangements of letters or numbers, or a one-dimensional or two-dimensional bar code or some other pattern that identifies the manufacturer of the surgical instrument, the manufacturer of the surgical guide, the manufacturer of the surgical system, including the robotics associated therein, or an authorized licensee of such manufacturers, depending on which entity desires to control surgical access. The pattern may also identify instrument type, so as to be able to allow or block certain types of surgical instruments. The pattern may be laser or chemical etched on the surface of the surgical instrument or otherwise printed thereon. The printing may be performed by a surgical instrument manufacturer before selling the instrument or by an authorized user of the surgical system before performing the surgical procedure (using an authorized printer and/or authorized printing software). The pattern may also include calibration marks so that the translation and rotation sensor may be synchronized with those marks in order to improve precision. It is preferable that the identifying pattern cannot be copied by an unauthorized entity.

Instead of or in addition to using a pattern or marking on the surface of the surgical instrument, inductive and/or capacitive sensing could be used to identify an authorized instrument. In this embodiment, the reader may read the inductive and/or capacitive identification.

Instead of or in addition to using a pattern or marking on the surface of the surgical instrument, the system may use a radio-frequency identification (RFID) tag to identify authorized surgical instruments. In this embodiment, the surface reader may also include an RFID reader that may detect the RFID tag embedded in or on the surgical instrument.

The benefit of this function of the surface reader is to prevent the use of unauthorized surgical instruments with a surgical system or surgical guide. Unauthorized instruments may not have the same quality or precision as that of authorized instruments and thus may pose a danger to a patient during surgery, may not work as well as authorized instruments, or may not be able to take advantage of all the benefits of the surgical system. Unauthorized instruments may also not be calibrated, such that the surgical system cannot determine how far the instrument has traveled or whether the instrument has been rotated.

The various embodiments of system 10 described above using sensorized surgical guides 16, 16a, 16b, and 16c are not limited to any specific procedure and may be used in a variety of surgical procedures. For example, system 10 may be used for bone edema procedures. Depending on the procedure, sensorized surgical guides 16, 16a, 16b, and 16c may be used with a variety of surgical instruments including, but not limited to, trocars, cannulas, scissors, probes, lasers, monopolar RF, bipolar RF or multipolar RF devices, graspers, forceps, electro-surgical knives, ultrasonic transducers, cameras, and the like. Surgical system 10 may also be used with other medical imaging systems such as MRI.

The above discussion is meant to illustrate the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. A surgical system comprising:
a bed extending along a main direction, the bed having a table top to support a patient;
a robotic arm disposed adjacent to the bed and controllable to move in relation to the body of the patient; and
a surgical guide attached to the robotic arm, the surgical guide capable of holding a surgical instrument and measuring a translation of the surgical instrument as it moves through the surgical guide, wherein:

the robotic arm is configured to position the surgical guide to a desired position in relation to a target area of the patient; and the surgical guide includes:

a reader for determining whether the surgical instrument is authorized; and a shutter assembly in communication with the reader, wherein the shutter assembly comprises a piston controlled by a solenoid, and the solenoid is energized to move the piston to allow the surgical instrument to be fed through the surgical guide.

2. The system of claim 1, further comprising a radiological imaging system including a source suitable to emit radiation that passes through at least part of the patient, the radiation defining a central axis of propagation, and at least one detector suitable to receive the radiation, wherein the source and detector define an analysis zone in which the at least part of the patient is placed.

3. The system of claim 1, further comprising a system computer in communication with the robotic arm, wherein the system computer includes navigational software to control the positioning of the robotic arm and the surgical guide.

4. The system of claim 1, wherein the reader is configured to read markings on the surgical instrument when the surgical instrument is fed through the surgical guide.

5. The system of claim 1, wherein the reader is configured to read a radio-frequency identification tag on the surgical instrument when the surgical instrument is fed through the surgical guide if it is determined that the surgical instrument is authorized.

6. The system of claim 1, wherein the surgical guide includes a proximal section connected to a distal section that is connected to the robotic arm, the proximal section includes a proximal guide, and the distal section includes a distal guide.

7. The system of claim 6, wherein the proximal section rotates in relation to the distal section to place the surgical guide in an open configuration and a closed configuration, and in the closed configuration the proximal and distal sections are aligned with one another.

8. The system of claim 6, wherein the proximal guide and the distal guide include ball bearings.

9. The system of claim 6, wherein the proximal guide includes a reader for detecting the translation of the surgical instrument.

10. The system of claim 9, wherein the reader detects rotation of the surgical instrument.

11. The system of claim 6, wherein the proximal guide includes a reader for determining whether the surgical instrument is authorized.

12. The system of claim 11, wherein the reader is configured to read markings on the surgical instrument when the surgical instrument is fed through the surgical guide.

13. The system of claim 6, further comprising a distance sensor disposed on the distal section of the surgical guide to monitor the distance between the surgical guide and the patient.

14. The system of claim 6, further comprising a depth indicator disposed on the surgical guide to indicate the depth the surgical instrument has been inserted into the patient.

* * * * *